United States Patent [19]

Satou

[11] Patent Number: 5,223,639
[45] Date of Patent: Jun. 29, 1993

[54] PROCESS FOR PRODUCING N-(3′, 4′-DIMETHOXYCINNAMOYL)-ANTHRANILIC ACID

[75] Inventor: Masashi Satou, Saiki, Japan

[73] Assignee: Kohjin Co., Ltd., Tokyo, Japan

[21] Appl. No.: 684,936

[22] PCT Filed: Nov. 5, 1990

[86] PCT No.: PCT/JP90/01436
§ 371 Date: Jun. 7, 1991
§ 102(e) Date: Jun. 7, 1991

[87] PCT Pub. No.: WO91/06528
PCT Pub. Date: May 16, 1991

[30] Foreign Application Priority Data

Nov. 6, 1989 [JP] Japan ................................ 1-287602

[51] Int. Cl.⁵ .......................................... C07C 229/56
[52] U.S. Cl. ...................................... 562/455; 560/45
[58] Field of Search ........................... 562/455; 560/45

[56] References Cited

U.S. PATENT DOCUMENTS

| Re. 32,944 | 6/1989 | Harita et al. | 562/455 |
| 4,026,896 | 5/1977 | Harita et al. | 562/455 |
| 4,337,270 | 6/1982 | Noda et al. | 560/45 |
| 4,587,356 | 5/1986 | Iizuka et al. | 562/455 |
| 5,049,572 | 9/1991 | Scherrer et al. | 562/455 |

Primary Examiner—José G. Dees
Assistant Examiner—B. Frazier
Attorney, Agent, or Firm—Oliff & Berridge

[57] ABSTRACT

A process for producing N-(3′,4′-dimethoxycinnamoyl)-anthranilic acid, which comprises (i) allowing 3′,4′-dimethoxycinnamic acid to react with anthranilic acid in an aprotic polar solvent in the presence of a particular inorganic salt and an iminium salt—which could be prepared quantitatively from dimethylformamide and an inexpensive acid halide—or (ii) allowing 3′,4′-dimethoxycinnamic acid to react with an iminium salt and then with an anthranilic acid-inorganic salt complex, a novel complex not described in the literature. According to the process of this invention, the desired compound can be produced in a high yield with no substantial formation of hardly separable by-products.

5 Claims, 2 Drawing Sheets

PROCESS FOR PRODUCING N-(3', 4'-DIMETHOXYCINNAMOYL)-ANTHRANILIC ACID

BACKGROUND OF THE INVENTION

1. Field of the Invention

The present invention relates to a process for producing N-(3',4'-dimethoxycinnamoyl)-anthranilic acid, a compound useful as a medicament for treating diseases caused by allergy, and more particularly to a process for producing the compound in a high yield in an industrially advantageous manner.

2. Description of Prior Art

N-(3',4'-dimethoxycinnamoyl)-anthranilic acid can be produced by various methods, including those in which 3',4'-dimethoxycinnamic acid or a derivative thereof is condensed with anthranilic acid or an ester thereof. Among hitherto known methods involving condensation are:

A) A process in which a reactive derivative of 3',4'-dimethoxy-cinnanic is condensed with anthranilic acid (see, e.g., Japanese Patent Publication No. 40,710/81 and Japanese Patent Application (Laid Open) No. 32,756/85);

B) A process in which a reactive derivative of N-(3',4'-dimethoxycinnamoyl)-anthranilic is condensed with an ester of anthranilic acid, followed by the hydrolysis of the ester (see, e.g., Japanese Patent Publication No. 36,905/82);

C) A process in which 3',4'-dimethoxycinnamic acid is condensed with anthranilic acid or an ester thereof in the presence of a condensing agent (see, e.g., Japanese Patent Publication No. 48,545/83); and D) A method in which 3',4'-dimethoxycinnamic acid is reacted with anthranilic acid in the presence of excess condensing agent to form [2-(3',4'-dimethoxystyryl)-3,1-benzoxazin-4-one] followed by the hydrolysis thereof (see, e.g., Japanese Patent Publication No. 3,995/84).

In processes A and B mentioned above, 3',4'-dimethoxycinnamic acid must be converted into a reactive derivative prior to condensation. The processes therefore require complicated operations. In addition, the processes involve a heating reaction during which by-products are formed through side reactions and decomposition of raw materials, and hence the yield of the desired compound becomes lower. There are even cases where a hardly separable by-product, 2-(3',4'-dimethoxystyryl)-3,1-benzoxazodin-4-one, is formed. In such cases, complicated purification steps are required. Process B, which utilizes an ester of anthranilic acid, is also disadvantageous in that it requires such additional steps as hydrolysis of the ester group and desalination with an acid.

Process C is advantageous in that there is no need for the conversion into a reactive derivative. However, when anthranilic acid is employed as a starting material and a condensing agent is used in around stoichiometric quantity, the desired compound could hardly be obtained because of undesirable side reactions. The process is therefore practiced by using a condensing agent in an amount less than stoichiometrically required, preferably ca. 0.4 times the quantity required stoichiometrically. It is therefore inevitable that the desired product can be produced at a low yield. In addition, by-products are still formed in large quantities including those which could hardly be separated, and hence the process requires complicated purification steps.

Process D was proposed as a method for overcoming such disadvantages. However, it is still unsatisfactory as an industrial process since the desired product could not be produced directly and hence complicated operation is required. In addition, the yield of the desired product is still not high owing to by-products.

DESCRIPTION OF THE INVENTION

The present inventors have conducted intensive studies in order to overcome the above disadvantages. As a result, it has now been found that the desired N-(3',4'-dimethoxycinnamoyl)-anthranilic acid can be obtained in a high yield by reacting 3',4'-dimethoxycinnamic acid with anthranilic acid in an aprotic polar solvent in the presence of an iminium salt and an inorganic salt, and that N-(3',4'-dimethoxycinnamoyl)-anthranilic acid so obtained can be purified quite easily since it is almost free from by-products.

Accordingly, there is provided by the present invention a process for producing N-(3',4'-dimethoxycinnamoyl)-anthranilic acid, represented by Formula [I] of the following:

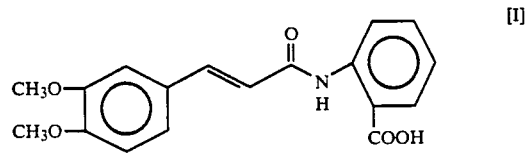

which comprises reacting 3',4'-dimethoxycinnamic acid with anthranilic acid in an aprotic polar solvent in the presence of an inorganic salt and an iminium salt (Vilsmeir Reagent) formed from dimethylformamide and an acid halide-type reagent.

Examples of acid halide-type reagents usable in this invention, are thionyl chloride, acetyl chloride, benzoyl choride, cyanuric chloride and phosphorus oxychloride. Of these reagents, thionyl chloride and phosphorus oxychloride can be preferable.

In this invention, acid halide type reagents are used preferably in around stoichiometric quantity, for example, in an amount of from 0.9 to 1.2 moles, per mole of the starting material, 3',4'-dimethoxycinnamic acid.

Various inorganic salts can be used in this invention. Examples of preferable inorganic salts include halides of alkaline earth metals, such as magnesium chloride, calcium chloride and magnesium bromide. Such inorganic salts are used preferably in an amount of 1 to 5 moles, per mole of anthranilic acid.

The process of this invention is practiced in an aprotic polar solvent. As examples of aprotic polar solvents usable in this invention, mention may be made of dimethylformamide, dimethylacetamide and dimethylsulfoxide. Of these solvents, dimethylformamide can be preferable. The reaction may be carried out at a temperature of 0° to 50° C. The period of time required for the reaction may be in the range of a few minutes to several hours, although it may vary depending on reaction conditions.

In practicing the process of this invention, a complex between anthranilic acid and an inorganic salt may be formed prior to the condensation, and the complex so formed may be used therefor. Such a complex can be readily formed by reacting anthranilic acid with an inorganic salt in the presence of a solvent. As examples of solvents usable for the formation of such a complex, mention may be made of acetonitrile, ethyl acetate, acetone and dimethylformamide. The reaction may be carried out at a temperature between room temperature and the boiling point of the solvent used. The period of time for the reaction may be in the range of ca. 0.5 to ca. 24 hours, although it depends on reaction conditions. After the completion of the reaction, crystals of the complex may be collected by filtration, and the crystals so obtained may be added to the reaction system to carry out the condensation according to this invention. The condensation utilizing such a complex may be effected in the presence of an additional inorganic salt, such as those described hereinabove.

Alternatively, such a complex may be formed in a solvent usable for the condensation, and the reaction mixture per se may be added to the reaction system. It is also possible to carry out the condensation in the reaction mixture, without isolating the complex.

The reaction between an iminium salt and 3',4'-dimethoxycinnamic acid is effected in a polar solvent, such as dimethylformamide, dimethylacetamide and dimethylsulfoxide, as described hereinabove. Reaction temperature may be in the range of 0° to 50° C. The period of time for the reaction may be in the range of from a few minutes to ca. 1 hour, although it depends on reaction conditions.

After the completion of the reaction, water may be added to the reaction mixture, so as to precipitate crystals of the desired N-(3',4'-dimethoxycinnamoyl)-anthranilic acid. The compound can be recovered by means of filtration. If necessary, crystals so obtained can be recrystallized from an appropriate solvent, for example, ethanol or ethanol-water, so as to obtain a purer product.

BEST MODES FOR PRACTICING THE INVENTION

Figure 1:
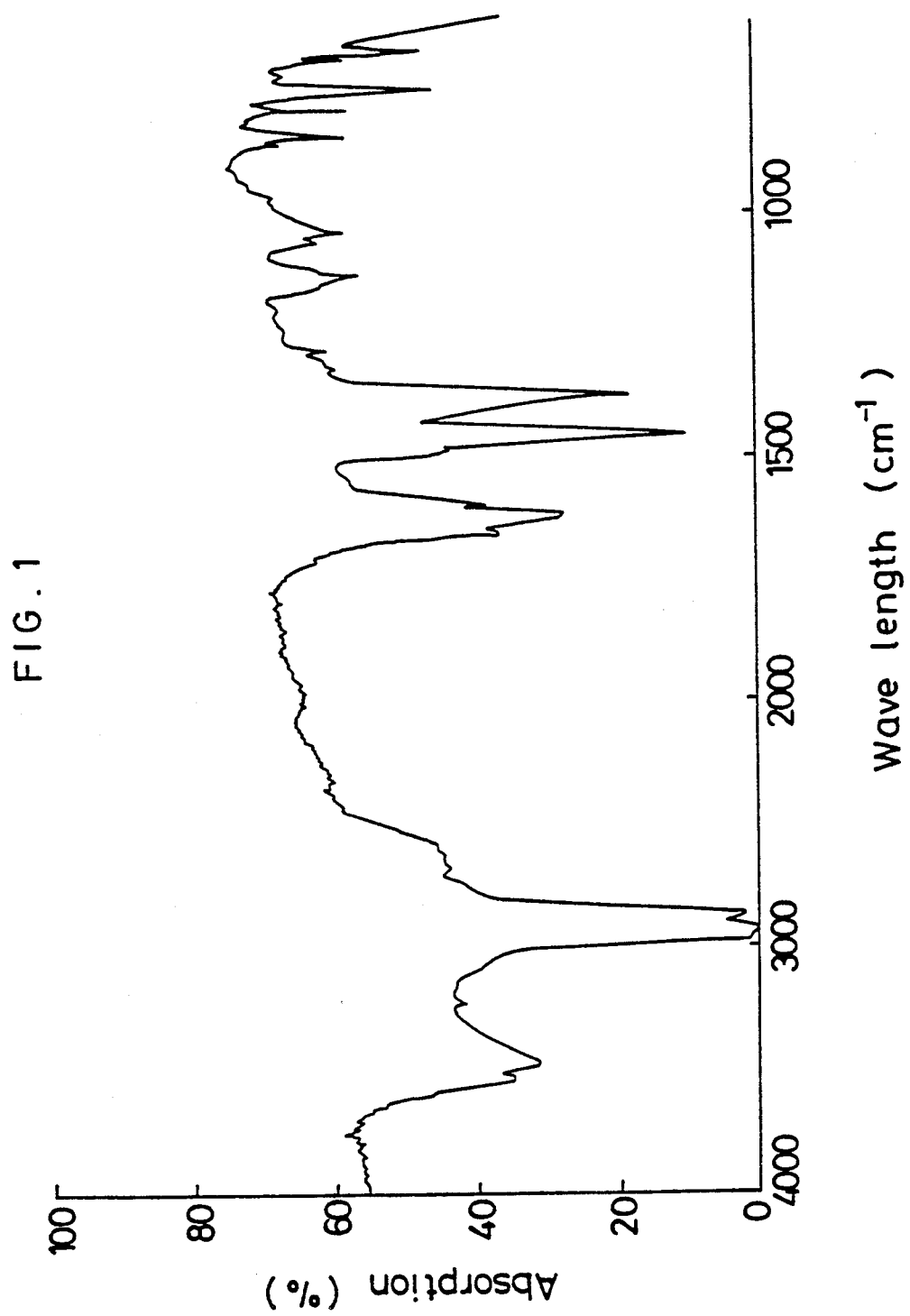
FIG. 1 shows an infrared absorption spectrum (nujor method) of anthranilic acid-magnesium chloride complex obtained in Reference Example 1.

This invention will further be illustrated by examples.

EXAMPLE 1

Into 15 ml of dimethylformamide were dissolved with heating 2.0 g of anthranilic acid and 2.3 g of anhydrous calcium chloride. To 10 ml of dimethylformamide were added in order 0.78 ml of thionyl chloride and 2.08 g of 3',4'-dimethoxycinnamic acid, during which the reaction system was stirred and cooled with ice and water. The resulting mixture was added dropwise to the above solution, during which the reaction system was stirred and cooled with ice and water. After the completion of the dropping, the reaction mixture was stirred for 30 minutes at the same temperature and then for 1 hour at room temperature. After the completion of the reaction, 80 ml of ice-water mixture was added thereto. Then, air was introduced thereinto for 30 minutes, and crystals deposited were collected by filtration and recrystallized from ethanol-water (1:2) to give 2.35 g (yield: 71.8%) of N-(3',4'-dimethoxycinnamoyl)-anthranilic acid. Melting point: 209°-211° C.

When the reaction mixture was subjected to thin layer chromatography (CHCl$_3$:MeOH=9:1), there appeared no spot corresponding to the by-product, (2-(3',4'-dimethoxystyryl)-3,1-benzoxazin-4-one).

The compound obtained above was identified by means of mixed melting point test with a standard sample and by means of infrared absorption spectrometry.

Reference Example 1

Into 100 ml of ethyl acetate was dissolved 6.9 g of anthranilic acid, and 4.8 g of anhydrous magnesium chloride was added thereto. The resulting mixture was stirred overnight at room temperature, and crystals deposited were collected by filtration to give 11.2 g of anthranilic acid-magnesium chloride complex.

It was proved by elementary analysis that the product had a composition of anthranilic acid:magnesium chloride = 1:1.

Elementary Analysis (found):
C: 36.47%
Mg: 10.18%
Cl: 28.54%

Figure 2:
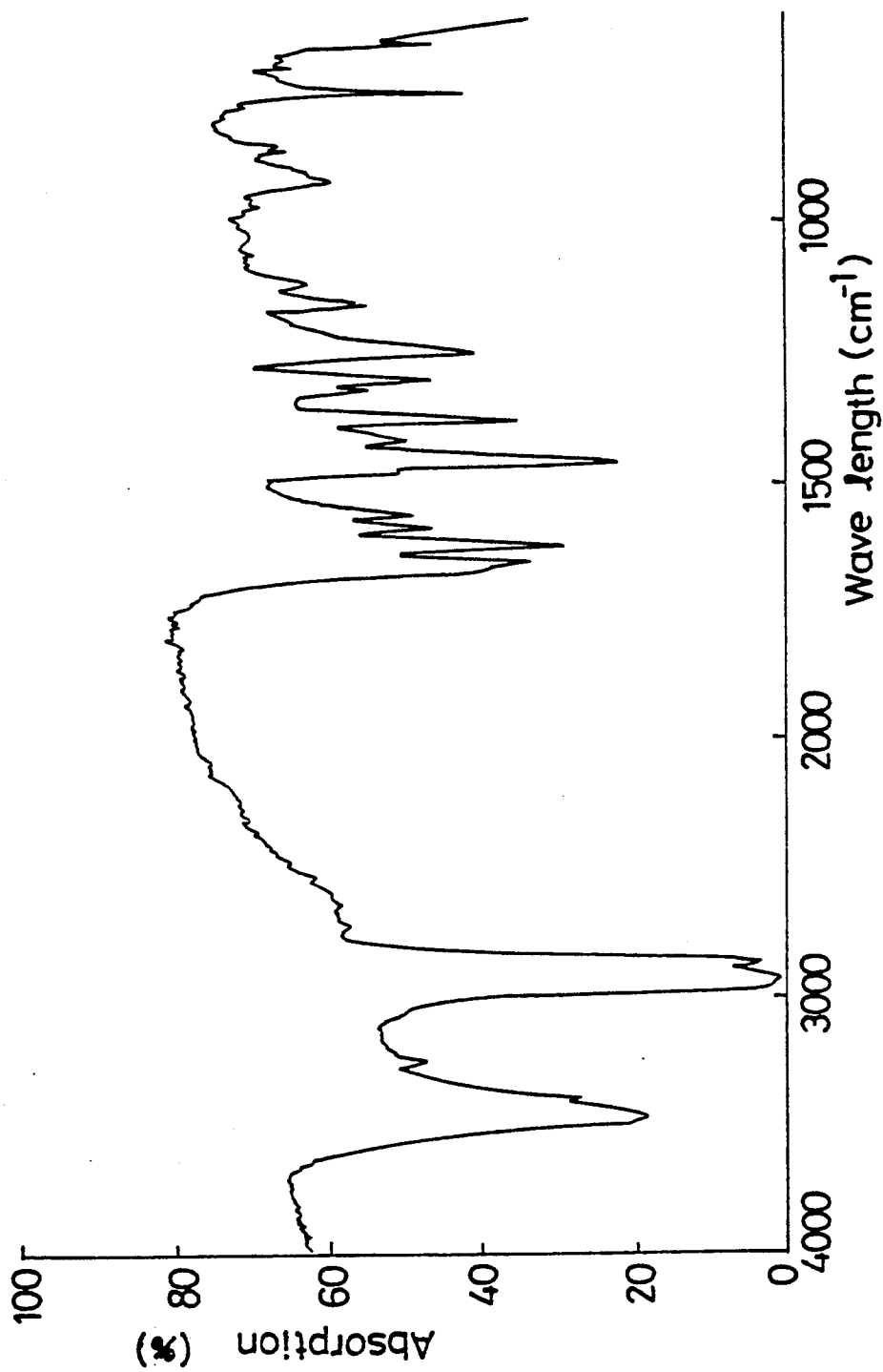
FIG. 2 shows an infrared absorption spectrum (nujor method) of a mixture of anthranilic acid and magnesium chloride, which was taken as a control for the complex of Reference Example 1.

IR Absorption Spectra:
There were taken infrared absorption spectra of the anthranilic acid-magnesium chloride (anhydrous) complex obtained above and of a simple mixture of anthranilic acid and an anhydrous magnesium chloride. The chart of the former is shown in FIG. 1, and that of the latter in FIG. 2. In FIG. 2 (simple mixture), there are observed peaks characteristics of respective compounds (3640, 3520, 1660 and 1620 cm$^{-1}$), whereas in FIG. 1 are observed quite different peaks (3500, 1700-1550, and 1300-800cm$^{-1}$). This proves that the complex is not a mere mixture of the two component.

EXAMPLE 2

Into 15 ml of dimethylformamide was dissolved with heating 4.65 g (0.02 mol) of anthranilic acid-magnesium chloride complex. To 10 ml of dimethylformamide were added in order 0.78 ml of thionyl chloride and 2.08 g (0.01 mol) of 3',4'-dimethoxycinnamic acid, during which the reaction system was stirred and cooled with ice and water. After being stirred for additional 15 minutes, the resulting mixture was added dropwise to the solution of anthranilic acid-magnesium chloride complex. After the completion of the dropping, the reaction mixture was stirred for 30 minutes at the same temperature and then for 1 hour at room temperature. After the completion of the reaction, 80 ml of ice-water mixture was added thereto. Then, air was introduced thereinto for 30 minutes, and crystals deposited were collected by filtration and recystallized from ethanol-water (1:3) to give 2.58 g (78.9%) of N-(3',4'-dimethoxycinnamoyl)-anthranilic acid. Molting point: 209°-211° C.

The compound was identified by means of mixed melting point test with a standard sample and by means of infrared absorption spectrometry.

When the reaction mixture was subjected to thin layer chromatography (CHCl$_3$:MeOH=9:1), there appeared no spot corresponding to the by-product, (2-(3',4'-dimethoxystyryl)-3,1-benzoxazin-4-one).

EXAMPLE 3

Into 15 ml of dimethylformamide were dissolved with heating 2.06 g (0.015 mol) of anthranilic acid and 2.7 g of magnesium chloride (anhydrous), and the resulting solution was cooled to room temperature. To 10 ml of dimethylformamide were added in order 0.78 ml of thionyl chloride and 2.08 g (0.01 mol) of 3',4'-dimethoxycinnamic acid, during which the reaction system was stirred and cooled with ice and water. After being stirred for additional 15 minutes, the resulting mixture was added dropwise to the above solution, with stirring at room temperature. After the completion of the dropping, the reaction mixture was stirred for additional 1.5 hours, and then treated in the same manner as in Example 2. There was obtained 2.48 g (yield: 75.8%) of N-(3',4'-dimethoxycinnamoyl)-anthranilic acid. Melting point: 209°–211° C.

The product was identified in the same manner as in Example 2.

When the product was subjected to thin layer chromatography (CHCl$_3$:MeOH=9:1), there appeared no spot corresponding to the by-product, (2-(3',4'-dimethoxystyryl)-3,1-benzoxazin-4-one).

EXAMPLE 4

Into 15 ml of dimethylformamide were dissolved with heating 1.37 g (0.01 mol) of anthranilic acid and 3.2 g of magnesium chloride (anhydrous), and the resulting solution was cooled to room temperature. To 10 ml of dimethylformamide were added in order 0.78 ml of thionyl chloride and 2.08 g (0.01 mol) of 3',4'-dimethoxycinnamic acid, during which the reaction system was stirred and cooled with ice and water. After being stirred for additional 15 minutes, the resulting mixture was added dropwise to the above solution, with stirring at room temperature. After the completion of the dropping, the reaction mixture was stirred for additional 1.5 hours, and then treated in the same manner as in Example 2. There was obtained 2.71 g (yield: 82.9%) of N-(3',4'-dimethoxycinnamoyl)-anthranilic acid. Melting point: 209°–211° C.

The product was identified in the same manner as in Example 2.

When the product was subjected to thin layer chromatography (CHCl$_3$:MeOH=9:1), there appeared no spot corresponding to the by-product, (2-(3',4'-dimethoxystyryl)-3,1-benzoxazin-4-one).

EXAMPLE 5

Into 15 ml of dimethylformamide were dissolved with heating 2.06 g (0.015 mol) of anthranilic acid and 3.2 g of magnesium chloride (anhydrous), and the resulting solution was cooled to room temperature. To 10 ml of dimethylformamide were added in order 0.78 ml of thionyl chloride and 2.08 g (0.01 mol) of 3',4'-dimethoxycinnamic acid, during which the reaction system was stirred and cooled with ice and water. After being stirred for additional 15 minutes, the resulting mixture was added dropwise to the above solution, with stirring at room temperature. After the completion of the dropping, the reaction mixture was stirred for additional 1.5 hours, and then treated in the same manner as in Example 1. There was obtained 2.99 g (yield: 91.3%) of N-(3',4'-dimethoxycinnamoyl)-anthranilic acid. Melting point: 209°–211° C.

The product was identified in the same manner as in Example 2.

When the product was subjected to thin layer chromatography (CHCl$_3$:MeOH=9:1), there appeared no spot corresponding to the by-product, (2-(3',4'-dimethoxystyryl)-3,1-benzoxazin-4-one).

Comparative Example 1

Into 15 ml of dimethylformamide were dissolved 1.51 g (0.011 mol) of anthranilic acid and 1.6 g of pyridine. To 10 ml of dimethylformamide were added in order 0.78 ml of thionyl chloride and 2.08 g (0.01 mol) of 3',4'-dimethoxycinnamic acid, during which the reaction system was stirred and cooled with ice and water. The resulting mixture was added dropwise to the above solution, during which the reaction system was stirred and cooled with ice and water. After the completion of the dropping, the reaction mixture was stirred for 30 minutes at the same temperature and then for 1 hour at room temperature. After the completion of the reaction, 80 ml of ice-water mixture was added thereto. The, air was introduced thereinto for 30 minutes, and crystals deposited were collected by filtration and recrystallized from chloroform to give 1.33 g (yield: 40.7%) of N-(3',4'-dimethoxycinnamoyl)-anthranilic acid.

Comparative Example 2

To 15 ml of dimethylformamide was dissolved 2.06 g (0.015 mol) of anthranilic acid. To 10 ml of dimethylformamide were added in order 0.78 ml of thionyl chloride and 2.08 g (0.01 mol) of 3',4'-dimethoxycinnamic acid, during which the reaction system was stirred and cooled with ice and water. The resulting mixture was added dropwise to the above solution, with stirring at room temperature. After the completion of the dropping, the reaction mixture was stirred for additional 1.5 hours, and then treated in the same manner as in Example 1. There was obtained 1.26 g (yield: 38.5%) of N-(3',4'-dimethoxycinnamoyl)-anthranilic acid.

INDUSTRIAL AVAILABILITY

In accordance with the process of this invention, the desired compound, N-(3',4'-dimethoxycinnamoyl)-anthranilic acid, can be directly produced in a high yield without being accompanied by hardly separable by-products, by allowing 3',4'-dimethoxycinnamic acid to react with anthranilic acid in an aprotic polar solvent in the presence of a particular inorganic salt and an iminium salt—which could be produced quantitatively from dimethylformamide and inexpensive acid halide-type reagents—or by allowing 3',4'-dimethoxycinnamic acid to react with an iminium salt and then with a novel anthranilic acid-inorganic salt complex not described in the literature.

Iminium salts, it has been known, can be used for a variety of reactions, including formylation of aromatic compounds and unsaturated compounds, and amidation (see, e.g., Tetrahedron Letter, 1960 9). However, none of the reactions have been in general use since they are not particularly advantageous. As is shown in Comparative Examples 1 and 2, when the reaction of 3',4'-dimethoxycinnamic acid with anthranilic acid is performed under conditions according to prior art, the desired compound is produced in a low yield and undesirable by-products are formed in large quantities, as in the cases disclosed in Japanese Patent Publication Nos. 40,710/81 and 48,545/83.

On the contrary, in this invention, the desired compound can be obtained in a high yield without any substantial formation of hardly separable by-products, in spite of the fact that an acid is generated during the course of the condensation reaction and basic substances or amines are not used in a quantity necessary to fully neutralize the acid. This is a result totally unexpected from the prior art.

What is claimed is:

1. A process for producing N-(3',4'-dimethoxycinnamoyl)-anthranilic acid, represented by Formula I:

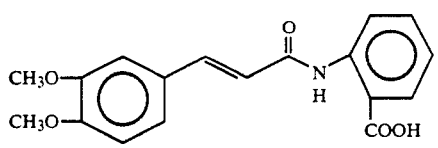

which comprises reacting 3',4'-dimethoxycinnamic acid with anthranilic acid in an aprotic polar solvent in the presence of an iminium salt and an inorganic salt, wherein said iminium salt is formed from dimethylformamide and an acid halide-type reagent, said acid halide-type reagent is present in an amount of about one mole per mole of 3',4'-dimethoxycinnamic acid, and wherein said inorganic salt is present in an amount ranging from 1 to 5 moles per mole of anthranilic acid; and said reaction occurring at a temperature between room temperature and a boiling point of said aprotic solvent.

2. A process for producing N-(3',4'-dimethoxycinnamoyl)-anthranilic acid represented by the following formula:

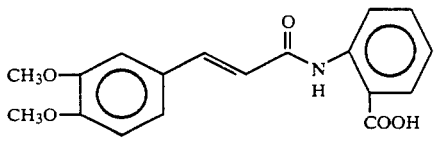

which comprises reacting 3',4'-dimethoxycinnamic acid with an iminium salt in the presence of an aprotic polar solvent at a temperature range of from 0° C. to 50° and then with an anthranilic acid-inorganic salt complex which is formed by reacting anthranilic acid with an inorganic salt in the presence of a solvent at a temperature between room temperature and the boiling point of the solvent.

3. A process as defined in claim 2, wherein said anthranilic acid-inorganic salt complex is an anthranilic acid-magnesium chloride complex.

4. A process as defined in claim 2, wherein, said reaction is carried out in the presence of an additional inorganic salt, in addition to the one contained in said complex.

5. A process as defined in claim 3, wherein said reaction is carried out in the presence of an additional inorganic salt, in addition to said salt contained in said complex.

* * * * *